(12) United States Patent
Roland et al.

(10) Patent No.: US 8,707,759 B2
(45) Date of Patent: Apr. 29, 2014

(54) FLUE GAS SENSOR WITH WATER BARRIER MEMBER

(75) Inventors: Marc W. Roland, Calgary (CA); Daniel J. Dempsey, Carmel, IN (US)

(73) Assignee: Carrier Corporation, Farmington, CT (US)

( * ) Notice: Subject to any disclaimer, the term of this patent is extended or adjusted under 35 U.S.C. 154(b) by 541 days.

(21) Appl. No.: 13/040,739

(22) Filed: Mar. 4, 2011

(65) Prior Publication Data

US 2011/0226039 A1 Sep. 22, 2011

Related U.S. Application Data

(60) Provisional application No. 61/314,686, filed on Mar. 17, 2010.

(51) Int. Cl.
*G01N 27/407* (2006.01)
*G01N 33/00* (2006.01)

(52) U.S. Cl.
USPC ............ 73/23.31; 73/31.05; 73/31.07

(58) Field of Classification Search
CPC G01N 27/403; G01N 27/407; G01N 27/4077
USPC ............ 73/23.31, 31.05, 31.06, 31.07
See application file for complete search history.

(56) References Cited

U.S. PATENT DOCUMENTS

| | | | | |
|---|---|---|---|---|
| 3,288,199 A | * | 11/1966 | Philippoff et al. ............... | 431/6 |
| 3,766,715 A | * | 10/1973 | Archer ............................. | 95/279 |
| 3,811,319 A | * | 5/1974 | Arnold ........................... | 73/31.07 |
| 4,256,985 A | * | 3/1981 | Goodson et al. ............... | 327/509 |
| 4,543,815 A | * | 10/1985 | Troup et al. .................. | 73/28.01 |
| 4,622,004 A | * | 11/1986 | Dalhuisen ........................ | 431/76 |
| 4,714,546 A | * | 12/1987 | Solomon et al. ............... | 210/137 |
| 4,745,796 A | * | 5/1988 | Abdelrahman et al. ...... | 73/31.07 |
| 4,957,522 A | * | 9/1990 | Brassell ............................. | 96/4 |
| 5,053,754 A | * | 10/1991 | Wong ............................ | 340/632 |
| 5,979,219 A | * | 11/1999 | Sellmer-Wilsberg et al. ............................ | 73/19.12 |
| 6,595,201 B2 | * | 7/2003 | Garloch et al. ............ | 126/116 A |
| 7,389,672 B2 | * | 6/2008 | Howard et al. .............. | 73/23.21 |
| 8,299,424 B2 | * | 10/2012 | Camilli ......................... | 250/288 |
| 2003/0145644 A1 | * | 8/2003 | Rabbett et al. ................. | 73/1.06 |
| 2003/0222010 A1 | * | 12/2003 | Bassett et al. ................. | 210/312 |
| 2008/0175759 A1 | * | 7/2008 | Oishi et al. ...................... | 422/98 |
| 2008/0282771 A1 | * | 11/2008 | Hamatani et al. ............ | 73/23.31 |
| 2009/0139496 A1 | * | 6/2009 | Rea et al. ...................... | 123/520 |
| 2010/0050761 A1 | * | 3/2010 | Lawrence et al. .......... | 73/152.28 |
| 2011/0174052 A1 | * | 7/2011 | Kuebel ......................... | 73/23.31 |

FOREIGN PATENT DOCUMENTS

WO   WO 2008/054382   *   5/2008

* cited by examiner

*Primary Examiner* — Daniel S Larkin

(74) *Attorney, Agent, or Firm* — Miller Malthias & Hull LLP

(57) ABSTRACT

A flue gas sensor of a combustion device is disclosed. The flue gas sensor may include a housing and a gas detector disposed within the housing, wherein the gas detector detects or measures at least one gas in a flue gas stream of the combustion device. The housing may also include a water barrier member through which the at least one gas comes into contact with the gas detector.

13 Claims, 4 Drawing Sheets

FLUE GAS SENSOR WITH WATER BARRIER MEMBER

CROSS-REFERENCE TO RELATED APPLICATIONS

This is a non-provisional U.S. patent application, which claims priority under 35 U.S.C. §119(e) to U.S. Provisional Patent Application Ser. No. 61/314,686 filed on Mar. 17, 2010, the entirety of which is incorporated by reference herein.

TECHNICAL FIELD OF THE DISCLOSURE

This disclosure generally relates to a method and apparatus for monitoring at least one gas in a flue gas stream and, more particularly, relates to the use of a water barrier member to prevent premature failure of flue gas sensors caused by water or water vapor in the flue gas stream.

BACKGROUND OF THE DISCLOSURE

Combustion devices based on hydrocarbon fuels are widely used to provide thermal, mechanical or electric energies. For example, fireplaces, ovens, furnaces, and boilers have been installed and used in commercial and residential buildings to provide heat, hot water, and other conveniences. Ideally, complete combustion occurs when hydrocarbon compounds in the fuel exothermically react with oxygen in the air to produce water vapor and carbon dioxide. Furnace systems are designed to run the combustion reaction with an excess of oxygen so that complete combustion can take place and maximum amount of heat may be released from hydrocarbon fuels.

On the other hand, a combustion reaction in which carbon monoxide (CO), a poisonous gas, is formed from a hydrocarbon is an incomplete combustion or a partial combustion. Incomplete combustion occurs when there is an insufficient amount of oxygen to react with the hydrocarbon. In addition, incomplete combustion can adversely affect the function of a combustion device, such as by decreasing its efficiency and heat output. CO is also formed from quenching a combustion process. Because of its possible adverse effects on the combustion device, it is desirable to monitor CO emissions continuously.

Traditionally, residential furnaces do not have a detection system for directly monitoring the concentration of carbon monoxide or other gasses present in combustion products due to feasibility including high cost and limited durability relative to a residential furnace. Pressure switches provide a mechanism to ensure proper airflow in furnaces. The pressure switches are only activated when a proper amount of airflow is reached. In the event of insufficient airflow the furnace shuts down. As a result, the pressure switches only deactivate the furnace system if there is an air blockage or starvation of combustion air.

Most commercially available gas sensors are generally not used in a flue gas stream of a combustion device. For example, hydrogen and helium sensors have been used in chiller tanks under negative pressure to detect any leakage existing on the exterior shell of the tanks. Similarly, household or industrial CO detectors based on liquid electrolyte are also known but generally operate at room temperature and are not suitable for use in most high temperature flue gas environment. Recently, smaller and less expensive CO sensors suitable for use in a flue gas stream, such as those disclosed in the co-pending U.S. Patent Application Publication No. 2010/0009304, have been developed and used in residential furnaces. Similar oxygen, carbon dioxide and hydrocarbon gas sensors are also functional for the purposes of detecting incomplete combustion.

One problem associated with existing flue gas sensors is premature sensor failure. For example, while the average design life of a residential furnace is about twenty years, existing flue gas sensors generally have a substantially shorter life span, with some sensor failure occurring within two to three years of operation. The disparity between the life of the sensor and that of the furnace not only requires frequent service or replacement of the sensor, but also significantly affect the safe operation of the furnace, especially toward the end of the furnace life when incomplete combustion and excessive CO emission are most likely to OMIT.

Hence, there is a need for a flue gas sensor with improved reliability and durability over existing sensors. Moreover, there is a need for a flue gas sensor having longer life spans than existing sensors without sacrificing its gas sensing performance.

SUMMARY OF THE DISCLOSURE

In satisfaction of the aforementioned needs, an improved flue gas sensor of a combustion device is disclosed. The flue gas sensor may include a housing and a gas detector disposed within the housing, wherein the gas detector detects or measures at least one gas in a flue gas stream of the combustion device. The housing may also include a water barrier member through which the at least one gas comes into contact with the gas detector.

In another aspect of this disclosure, a method for monitoring at least one gas in a flue gas stream of a combustion device is disclosed. The method may comprise the steps of providing a flue gas sensor in direct contact with the flue gas stream, the sensor comprising a housing enclosing a gas detector for the at least one gas, the housing including a water barrier member through which the at least one gas comes into contact with the gas detector; and allowing the gas detector to detect the at least one gas in the flue gas stream.

Other advantages and features of the disclosed sensor and method of use thereof will be described in greater detail below. It will also be noted here and elsewhere that the device or method disclosed herein may be suitably modified to be used in a wide variety of applications by one of ordinary skill in the art without undue experimentation.

BRIEF DESCRIPTION OF THE DRAWINGS

For a more complete understanding of the disclosed apparatus and method, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed device or method which render other details difficult to perceive may have been omitted. It should be understood, of course, that this disclosure is not limited to the particular embodiments illustrated herein.

DETAILED DESCRIPTION OF THE DISCLOSURE

This disclosure is generally directed to a method and apparatus for monitoring at least one gas in a flue gas stream of a combustion device. As mentioned earlier, one problem associated with current flue gas monitoring techniques is the premature failure of gas sensors. Without wishing to be bound by any particular theory, it is contemplated in this disclosure that at least a substantial portion of the hot water vapor of the flue gas may come in direct contact with a gas detector, thereby causing or significantly accelerating the corrosion of its vital components, such as electrodes, metal plates, wires, etc.

The hydrogen/helium sensors for chiller tanks discussed earlier in the background section may include a membrane that prevents water or water vapor from contacting the hydrogen/helium detector. The membrane there, however, would not be contemplated as a likely solution to the problem of premature flue gas sensor failure for several reasons. First, the membrane in the chiller operates in a low temperature, low pressure (on the order of 6 torr) and stationary environment, which is significantly different from a hot and moist flue gas stream. In fact, it is known that water vapor rapidly transpires through a gas porous membrane as temperature and humidity changes, which is identified in U.S. Pat. No. 5,338,429 (column 2, lines 40-68) as one of the major drawbacks in gas sensors utilizing such membranes. Moreover, even assuming the membrane used in the chiller can block water in a flue gas environment, the fact that it selectively allows hydrogen and helium (molecules significantly smaller than water molecules) to pass through does not in itself render it capable of selectively allowing $CO$, $CO_2$, $O_2$, etc (molecules equal to or larger than water molecules) to pass through the membrane to the gas detector.

According to one aspect of this disclosure, it is found that premature failure of flue gas sensors can be addressed by incorporating a temperature-tolerant membrane that selectively blocks at least a substantial portion of water or water vapor in a flue gas while allowing certain other components of the flue gas (e.g., $CO$, $CO_2$, $O_2$, $N_2$, and/or $NO_x$) to pass through to a corresponding gas detector.

Figure 1:
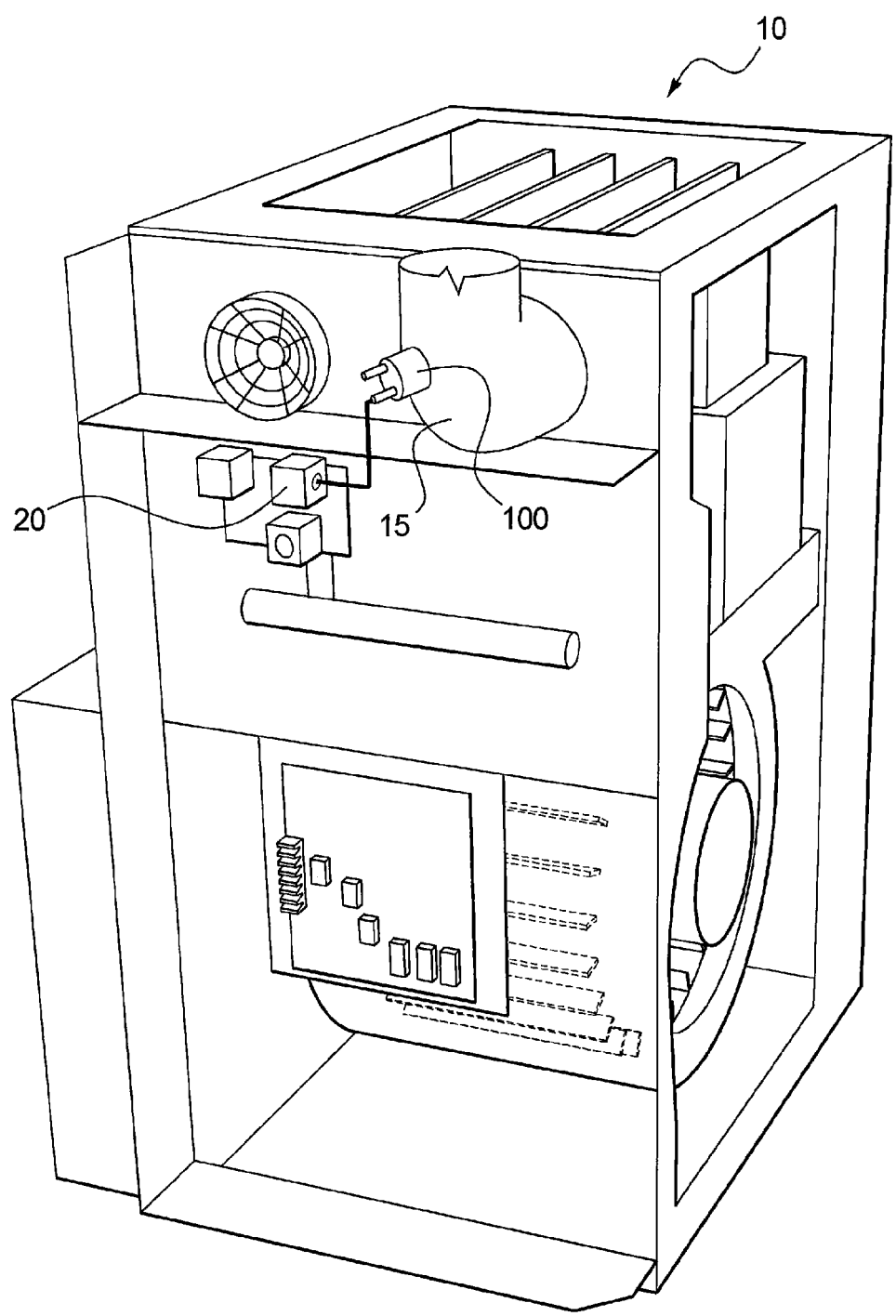
FIG. 1 is a front perspective view of a combustion device utilizing a flue gas sensor according to this disclosure, particularly illustrating the position of the sensor in direct contact with the flue gas stream.

Referring now to FIG. 1, an exemplary embodiment of an improved flue gas sensor generally referred to by reference numeral 100 is illustrated. The gas sensor 100 detects and/or measures the concentration of at least one gas in a flue gas stream of a combustion device (also referred herein as a furnace system) 10, such as a residential fossil fuel furnace or an oil burning appliance. Once the concentration of the gas indicates an incomplete combustion, the combustion device 10 may take a control action or shutdown to permit service to be performed or an external cause corrected.

The gas sensor 100 may be used in combination with a programmable machine 20 that is in operative communication with the gas sensor and the combustion device 10. The programmable machine 20 may take action as required, such as, for example, deactivating the combustion device 10 to permit service to be performed or the external cause corrected when a predetermined concentration of gas is reached. The gas constituent monitored may be oxygen, carbon dioxide, carbon monoxide, nitrogen, nitrous oxide, or combinations thereof. The predetermined concentration for carbon monoxide may be 50-1000 parts per million (ppm).

One example of the programmable machine 20 is a control processing unit (CPU). It is contemplated by this disclosure that the CPU may include computers, processors, microcontrollers, microcomputers, programmable logic controllers, application specific integrated circuits (ASIC), field programmable gate arrays (FPGA) and any other programmable circuits. It is further contemplated by this disclosure that the CPU is any number of control devices providing various types of control, e.g., centralized, distributed, redundant and/or remote control. The CPU could be connected to a furnace control board or remotely connected to a thermostat or other electronics. The CPU may also be integrated to the gas sensor 100 itself.

As illustrated in FIG. 1, the gas sensor 100 may be located inside a flue pipe 15 of the combustion device 10. However, the gas sensor 100 may be positioned anywhere within the combustion device 10 that is in communication with the flue gas. In order to ensure safe and efficient operation of the combustion device 10, the gas sensor 100 may operate, either continuously or at suitable time intervals according to safety regulations, during the entire combustion process.

Figure 2:
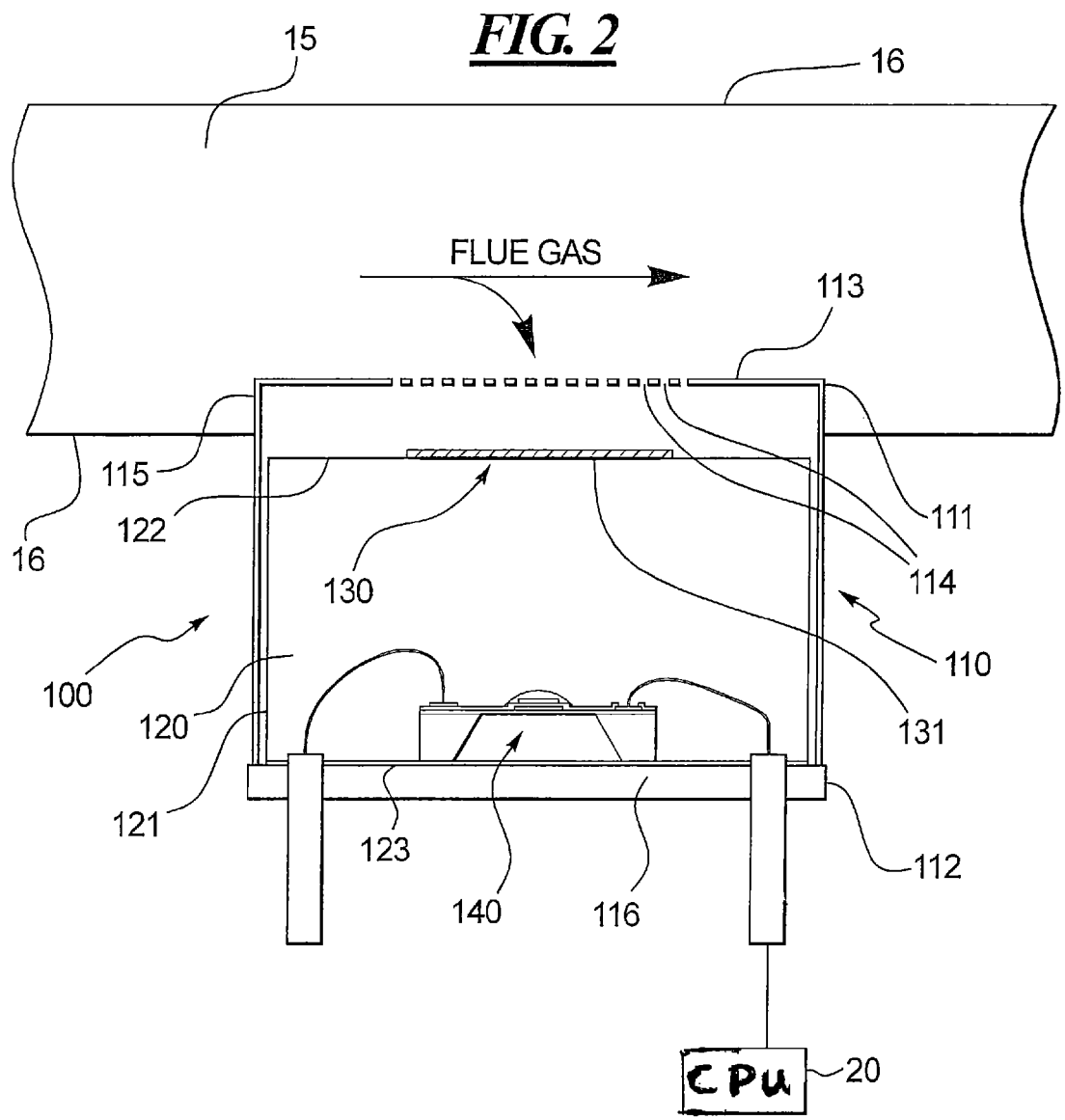
FIG. 2 is a schematic illustration of one embodiment of the flue gas sensor shown in FIG. 1.

Turning to FIG. 2, the disclosed gas sensor 100 may include a housing 110 and a gas detector 140 disposed within the housing for detecting or measuring at least one gas in a flue gas stream of the combustion device 10. The housing 110 may further include a water barrier member 130 through which the at least one gas comes in contact with the gas detector 140. As used herein, the term "proximal" or "upstream" refers to a direction towards the combustion device 10, and the term "distal" or "downstream" refers to a direction away from the combustion device.

The housing 110 extends through a sidewall 16 of the flue pipe 15 with a proximal end 111 that extends into the flue pipe and an opposing distal end 112 disposed outside of the flue pipe. However, it is to be understood that the proximal end 111 may also remain flush with the sidewall 16 of the flue pipe 15. As illustrated in FIG. 2, the distal end 112 may include a bottom wall 116 and the proximal end 111 may include an optional end wall 113 that may be in direct contact with the flue gas stream. The end wall 113 may include a plurality of transverse openings 114, through which the flue gas can enter into the housing 110. The openings 114 may be a plurality of circular holes, elongated slots, or openings of other shape or configurations known in the art. Although the openings 114 are shown in FIG. 2 as positioned on the end wall 113, it may also be additionally or alternatively positioned on an exterior sidewall 115 of the housing 110 that is inside of the flue pipe 15. In some embodiments, the housing 110 may not include any distal end wall, in which case the exterior sidewall 115 simply terminates into a distal opening (not shown). The housing 110 may be made of suitable materials known in the art, such as metal or plastic. Moreover, at least the portion of the housing 110 that is in direct contact with the flue gas should have sufficient structural integrity to prevent degradation of decomposition as a result of long term exposure to the high temperature flue gas.

The housing 110 may further include a detection chamber 120 in which the gas detector 140 is disposed. As illustrated in FIG. 2, the detection chamber 120 includes a chamber sidewall 121 extending between a chamber end wall 122 and a chamber bottom wall 123. Although the chamber sidewall 121 is illustrated in FIG. 2 as being separated from the exterior sidewall 115 of the housing 110, it should not be construed as limiting the scope of this disclosure as the sidewalls (121, 115) can be merged together in some embodiments. Similarly, the chamber bottom wall 123 may also be merged into the bottom wall 116 of the housing 110, instead of being separated therefrom as shown in FIG. 2.

Figure 3:
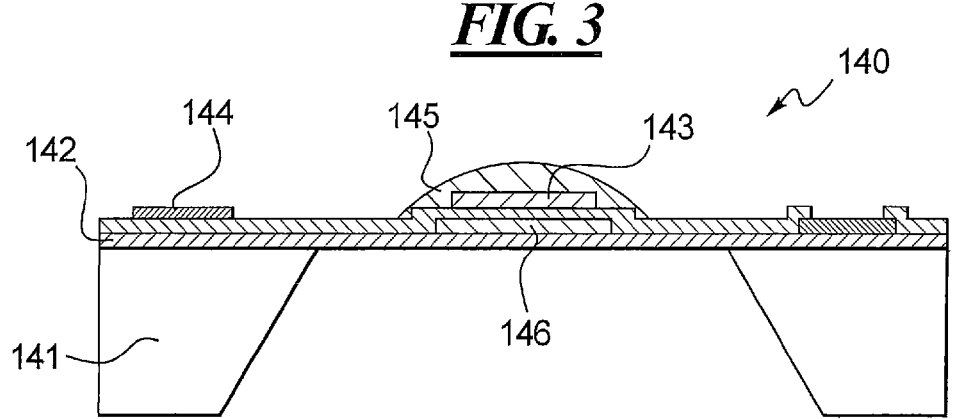
FIG. 3 is a schematic illustration of the gas detector used in the flue gas sensor shown in FIG. 2.

In order to monitor the flue gas, the gas detector 140 of the gas sensor 100 may be disposed in the housing 110. As illustrated in FIGS. 2-3, an embodiment of the gas detector 140 may include a base 141 supporting a temperature-tolerant top plate 142. The base 141 may be secured to the chamber bottom wall 123, such as through press-fitting, adhesives, fasteners, etc. Supported on the top plate 142 are central and peripheral electrodes 143 and 144, respectively. The central electrode 143 may be covered with a sensing layer 145, in which the at least one gas can be absorbed to cause a conductivity or resistance change between the respective central and peripheral electrodes 143 and 144. The peripheral electrode 144 may be electrically connected to the programmable machine 20.

The base 141 may be made of silicon or other suitable material. The top plate 142 may be made of silicon nitride ($Si_3N_4$) to provide thermal shock resistance, temperature endurance, and wear resistance. In one embodiment, the gas detector 140 may include an optional heating element (such as, a heater) 146 to maintain the detector at a temperature of at least about 100° C. so that condensation of water vapor on the detector 140 can be substantially reduced or prevented. It is to be understood, however, that the gas detector 140 suitable for use in the disclosed gas sensor 100 is not limited to the example shown in FIG. 3. Any detector that detects or measures flue gas concentrations, such as, for example, a metal oxide, mixed metal oxide, electrochemical, infrared or catalytic sensor, may be used in light of this disclosure. Preferably, the gas detector 140 is relatively inexpensive and easy to maintain and replace, as compared with a commercial analyzer, such as a GC-MS.

The gas detector 140 may be used to detect or measure at least one gas from the flue gas stream. For example, the at least one gas may be carbon monoxide, carbon dioxide, oxygen, nitrogen, nitrous oxide, or mixtures thereof. As used in this disclosure, the gas detector is not purported to detect or measure water or water vapor. The detection and measurement of the concentration of the at least one gas may indicate an incomplete combustion.

In order to prevent premature sensor failure caused by corrosion, the housing 110 further includes the water barrier member 130. Turning back to FIG. 3, the water barrier member 130 may be incorporated in the housing 110 in a number of configurations. For example, the water barrier member 130 may be formed as a part of the chamber end wall 122 as shown in FIG. 3. Alternatively, it may also be provided as a part of the chamber sidewall 121.

The water barrier member 130 may include a membrane 131 that is at least substantially permeable to the at least one gas and at least substantially impermeable to water or water vapor in the flue gas stream. For example, the membrane may have a microporous structure and/or a hydrophobic/hydrophilic property to allow it to selectively block water molecules while allowing similar size or bigger gas molecules, such as CO, $CO_2$, $O_2$, $N_2$, and/or $NO_x$ to pass through to the corresponding gas detector 140.

In one embodiment, the membrane 131 is made of ultra high molecular weight polyethylene (UHMWPE), available from ENTEK Membranes, 250 N. Hansard Ave., Lebanon, Oreg. 97355. Features of UHMWPE include a molecular weight of over three million grams per mole, extreme chain entanglement, natural abrasion resistance, hydrophobicity, and oleophilicity. The UHMWPE membrane used in this disclosure may have average pore sizes in the range of 25-1000 nanometers, with porosities ranging from 35% to 95%. Moreover, its thermal, acoustical, dielectric, and/or mechanical properties may be controlled by regulating the pore size and pore size distribution. For example, due to UHMWPE's high chain entanglement, a wide variety of different functional fillers, at varying concentrations, can be incorporated into the UHMWPE membrane. Suitable fillers include, but are not limited to, silica, calcium carbonate, activated carbon, carbon black, metals, such as copper and nickel powder.

In another embodiment, the membrane 131 may be made of sulfonated tetrafluoroethylene based fluoropolymer-copolymers, an ionomer known as Nafion®. Features of Nafion® include high temperature-endurance (up to 190° C.), chemical resistance, and water permeability based on temperature and pressure. For example, while Nafion® selective blocks water and water vapor in a flue gas environment, it can be highly permeable to water under other conditions.

Figure 4:
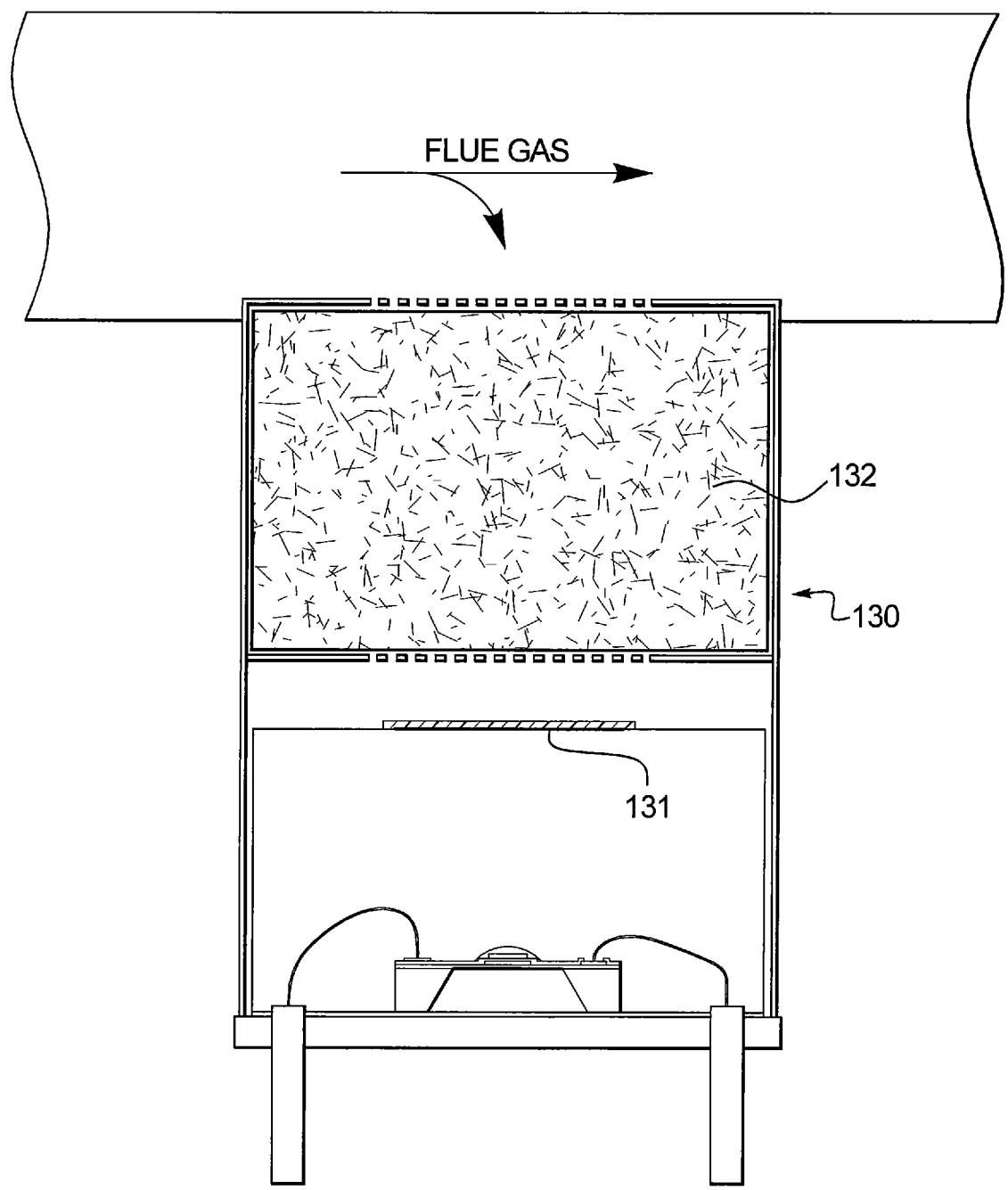
FIG. 4 is a schematic illustration of another embodiment of the flue gas sensor shown in FIG. 1, particularly illustrating the provision of a hydrocarbon filter layer.

Turning now to FIG. 4, the water barrier member 130 may further include a hydrocarbon filter layer 132 that is at least substantially impermeable to hydrocarbons in the flue gas stream. In one embodiment, the hydrocarbon filter layer 132 may comprise active carbon. In the embodiment shown in FIG. 4, the hydrocarbon filter layer 132 is positioned upstream to the membrane 131. In other embodiments, however, the filter layer 132 may be disposed downstream to, or even integrated with, the membrane 131 (not shown).

Figure 5:
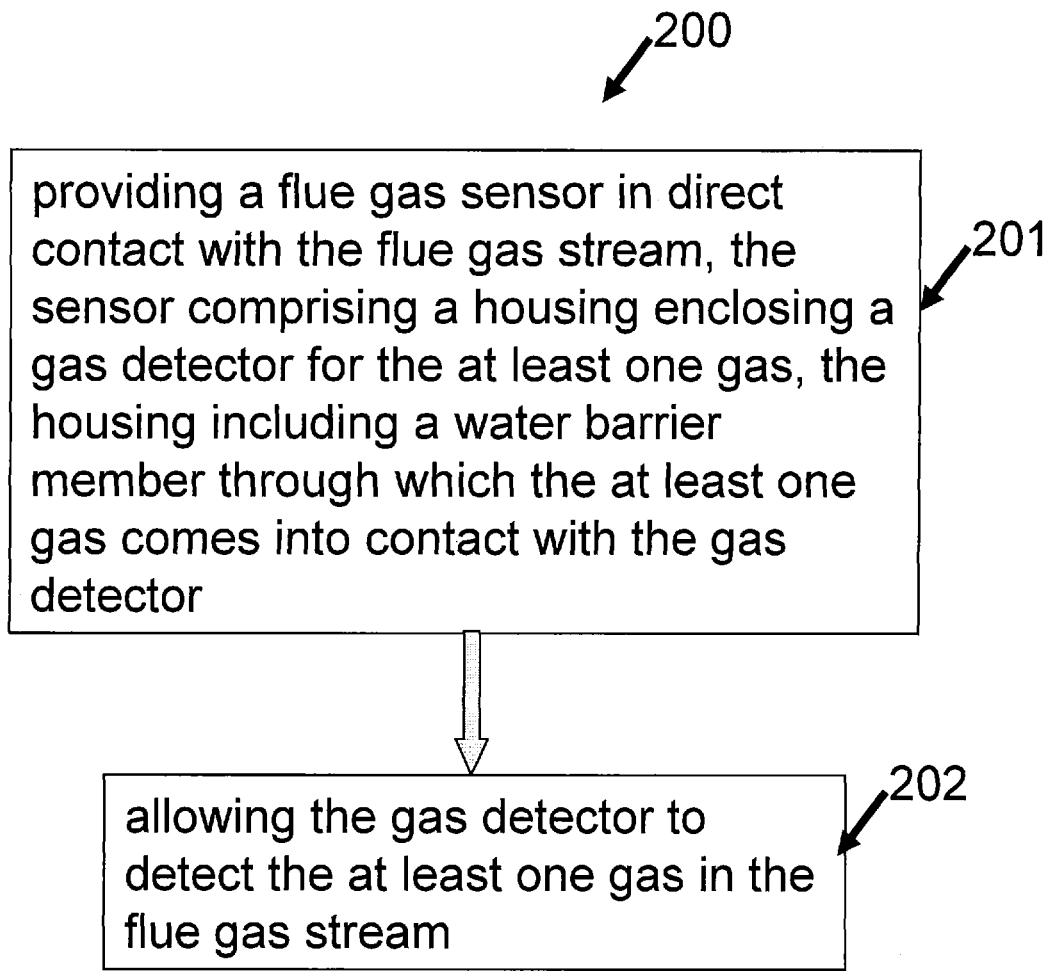
FIG. 5 is a block diagram of a method for continuously monitoring at least one gas in a flue gas stream of a combustion device according to another aspect of this disclosure.

In another aspect of this disclosure illustrated in FIG. 5, a method 200 for monitoring at least one gas in a flue gas stream of a combustion device is disclosed. The method 200 may comprise a step 201 of providing a flue gas sensor (such as the gas sensor 100) in direct contact with the flue gas stream, the sensor comprising a housing (such as the housing 110) enclosing a gas detector (such as the gas detector 140) for the at least one gas, the housing including a water barrier member (such as the water barrier member 130) through which the at least one gas comes into contact with the gas detector; and another step 202, which allows the gas detector to detect the at least one gas in the flue gas stream. In one embodiment, the gas detector continuously detects or measures the at least one gas during the entire operation of the combustion device.

INDUSTRIAL APPLICABILITY

The improved flue gas sensor disclosed herein may have a wide range of industrial, commercial or household applications. By using a barrier member that selectively blocks water and water vapor while allowing other gas to pass through to a gas detector, the durability and reliability of flue gas sensors can be significantly improved, especially when the sensor is continuously placed in a high temperature and a high moisture environment. Furthermore, by adding the water selective barrier member, the probability and severity of condensation within the gas sensor can be reduced. The disclosed sensor is relatively inexpensive and easy to maintain and replaced, without using complicated instruments, such as GC-MS.

While only certain embodiments have been set forth, alternative embodiments and various modifications will be apparent from the above descriptions to those skilled in the art. These and other alternatives are considered equivalents and within the spirit and scope of this disclosure.

What is claimed is:

1. A flue gas sensor of a combustion device, comprising:
a housing comprising a water barrier member;

a gas detector disposed within the housing, the gas detector detecting or measuring at least one gas in a flue gas stream of the combustion device, the at least one gas coming into contact with the gas detector through the water barrier member;

wherein the water barrier member comprises a membrane that is at least substantially permeable to the at least one gas and at least substantially impermeable to water or water vapor in the flue gas stream;

wherein the water barrier member further comprises a filter layer that is at least substantially impermeable to hydrocarbons in the flue gas stream; and wherein the membrane is positioned between the filter layer and a detection chamber.

2. The flue gas sensor of claim 1, wherein the at least one gas is selected from the group consisting of carbon monoxide, carbon dioxide, oxygen, nitrogen, nitrous oxide, and mixtures thereof.

3. The flue gas sensor of claim 1, wherein the combustion device is a residential fossil fuel furnace.

4. The flue gas sensor of claim 1, wherein the filter layer comprises active carbon.

5. The flue gas sensor of claim 1, wherein the membrane comprises a polymer material selected from the group consisting of polyethylenes, sulfonated tetrafluoroethylene based fluoropolymer-copolymers, and mixtures thereof.

6. The flue gas sensor of claim 1, wherein the gas detector further comprises a heating element.

7. The flue gas sensor of claim 6, wherein the gas detector is maintained at a temperature of at least about 100° C. by the heating element.

8. A method for monitoring at least one gas in a flue gas stream of a combustion device, the method comprising:

providing a flue gas sensor in direct contact with the flue gas stream, the flue gas sensor comprising a housing enclosing a gas detector for the at least one gas, the housing comprising a water barrier member through which the at least one gas comes into contact with the gas detector;

allowing the gas detector to detect the at least one gas in the flue gas stream;

wherein the water barrier member comprises a membrane that is at least substantially permeable to the at least one gas and at least substantially impermeable to water or water vapor in the flue gas stream;

wherein the water barrier member further comprises a filter layer that is at least substantially impermeable to hydrocarbons in the flue gas stream; and wherein the membrane is positioned between the filter layer and a detection chamber.

9. The method of claim 8, wherein the at least one gas is selected from the group consisting of carbon monoxide, carbon dioxide, oxygen, nitrogen, nitrous oxide, and mixtures thereof.

10. The method of claim 8, wherein the combustion device is a residential fossil fuel furnace.

11. The method of claim 8, wherein the filter layer comprises active carbon.

12. The method of claim 8, wherein the membrane comprises a polymer material selected from the group consisting of polyethylenes, sulfonated tetrafluoroethylene based fluoropolymer-copolymers, and mixtures thereof.

13. The method of claim 8, wherein the gas sensor further comprises a heating element.

* * * * *